United States Patent [19]

Davies

[11] Patent Number: 4,977,894
[45] Date of Patent: Dec. 18, 1990

[54] LARYNGO-TRACHEAL ANALGESIA ENDOTRACHEAL TUBE

[75] Inventor: Gerald G. Davies, Iowa City, Iowa

[73] Assignee: Sheridan Catheter Corporation, Argyle, N.Y.

[21] Appl. No.: 334,435

[22] Filed: Apr. 7, 1989

Related U.S. Application Data

[63] Continuation of Ser. No. 31,877, Mar. 30, 1987, abandoned.

[51] Int. Cl.⁵ ............................................. A61M 16/00
[52] U.S. Cl. .................................. 128/207.15; 604/96
[58] Field of Search ............. 128/343, 207.14–207.17; 604/96, 100, 101

[56] References Cited

U.S. PATENT DOCUMENTS

| 2,854,982 | 10/1958 | Pagano | 604/101 |
|---|---|---|---|
| 3,173,418 | 3/1965 | Baran | 128/207.15 |
| 4,114,625 | 9/1978 | Onat | 604/96 |
| 4,116,201 | 9/1978 | Shah | 128/207.15 |
| 4,180,076 | 12/1979 | Betancourt | 604/101 |
| 4,214,593 | 7/1980 | Imbruce et al. | 604/96 |
| 4,305,392 | 12/1981 | Chester | . |
| 4,446,864 | 5/1984 | Watson et al. | 128/207.14 |
| 4,543,089 | 9/1985 | Moss | 604/96 |
| 4,632,108 | 12/1986 | Geil | 128/207.14 |
| 4,637,389 | 1/1987 | Heyden | 128/207.15 |
| 4,642,092 | 2/1987 | Moss | 604/96 |
| 4,688,568 | 8/1987 | Frass et al. | 128/207.15 |
| 4,693,243 | 9/1987 | Buras | 604/96 |

FOREIGN PATENT DOCUMENTS 3303582  8/1983  Fed. Rep. of Germany ........................ 128/207.15

Primary Examiner—John D. Yasko
Assistant Examiner—Anthony Gutowski
Attorney, Agent, or Firm—Burns, Doane, Swecker & Mathis

[57] ABSTRACT

The laryngo-tracheal analgesia endotracheal tube is a modification of existing endotracheal tubes. It has the addition of an injection port to a lumen in the wall of the tube with exiting holes that correspond to the anatomical position of the epiglottis, larynx and trachea when the tube is correctly placed. The device allows for topical anesthesia to be applied to these pain sensitive areas on ititial placement and while the tube remains in place. The endotracheal tube of the present invention allows a patient to tolerate the presence of an endotracheal tube without discomfort and potentially dangerous reflexes of coughing, gagging, hypertension and tachycardia.

2 Claims, 1 Drawing Sheet

LARYNGO-TRACHEAL ANALGESIA ENDOTRACHEAL TUBE

This application is a continuation of application Ser. No. 031,877, filed Mar. 30, 1987.

BACKGROUND OF THE INVENTION

1. Field of the Invention

The present invention relates to endotracheal tubes, particularly laryngo-tracheal analgesia endotracheal tubes.

SUMMARY OF THE INVENTION

The invention described here is an improvement with additional uses of an endotracheal tube. The endotracheal tube of the present invention has the built in capability of topically anesthetizing the sensitive structures of the epiglottis, larynx and trachea when the tube is in place. An endotracheal tube incorporating modifications to allow deposition of local anesthetic during and after placement has never before been described or manufactured.

The tube incorporates a small lumen, for the purpose of drug administration, in the radially inward wall of an arcuate endotracheal tube. Local anesthetic injected through this lumen is deposited on and around the epiglottis, larynx and trachea. The advantage of topically anesthetizing these areas is that potentially dangerous reflexes of coughing, laryngospasm, hypertension and tachycardia can be prevented thereby facilitating safer anesthesia and patient management when endotracheal intubation is required.

DESCRIPTION OF THE PREFERRED EMBODIMENTS

Figure 1:
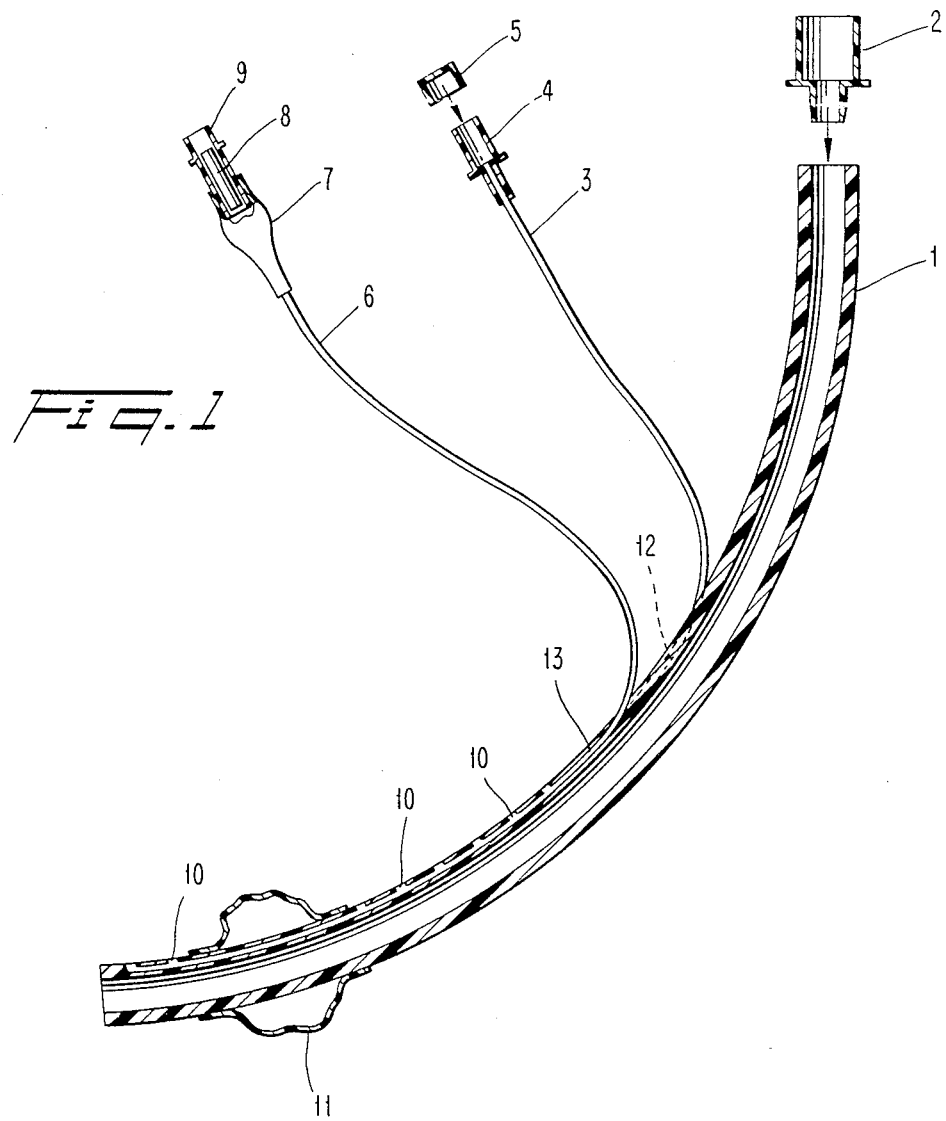
FIG. 1 is a longitudinal sectional view of an embodiment of the present invention.
Figure 2:
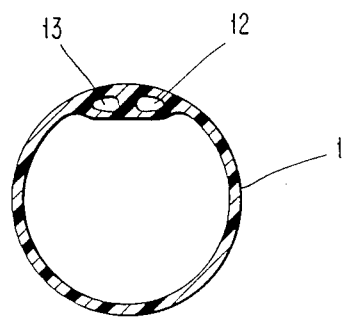
FIG. 2 is a cross-sectional view of an embodiment of the present invention showing the cuff inflation and drug administration lumens.

The invention described here is a modification with significant advantages and change of usage of a commonly used medical device called an endotracheal tube.

An endotracheal tube is a plastic or rubber, most commonly PVC, tube used for securing the airway of critically ill or anesthetized patients. Such a tube is necessary in order to perform mechanical positive pressure ventilation of the lungs and to prevent the possibility of aspiration or airway obstruction.

The larynx and trachea, through which this tube must pass, are amongst the most sensitive areas of the body. The presence of a tube in these structures invokes powerful reflexes of pain, coughing, gagging, retching and vomiting. It would be advantageous to administer a solution containing local anesthetic to the larynx and trachea on initial placement of the tube and subsequently as required while the tube is still in place, therefore preventing the pain, discomfort and potentially dangerous fits of coughing that might be produced by the presence of a tube in the larynx and trachea.

With presently available endotracheal tubes it is impractical to administer local anesthetic while the tube is in place. Removing the tube to administer local anesthetic is time consuming, difficult and occasionally dangerous.

The endotracheal tube of the present invention provides the ability to administer local anesthetic to the sensitive laryngo-tracheal area through a specially constructed side port (12) in the wall of the endotracheal tube (1).

The endotracheal tube of the present invention may be extruded from polyvinyl chloride and two small lumens (12,13) are incorporated in the side wall of the tube during the extrusion process. The wall thickness of the tube (1) is 1.5 mm expanded at the anterior aspect where the additional lumens (12,13) are formed. The tubes will eventually be manufactured with differing lengths and internal diameters in accordance with specifications of the American Standards Association.

Two small tubes (3,6) are cemented to the endotracheal tube (1) providing continuity with the lumens (12,13) in the endotracheal tube. The small tube (6) is connected to an airtight cuff (11). Air injected into this cuff provides an airtight seal of the trachea when the endotracheal tube is inserted in its proper anatomical position. The air volume of the cuff is controlled at the outer end of this tube by an injection adaptor (9), one way valve (8) and pilot balloon (7).

The second lumen of 1.5 mm diameter (12) serves as the route for administration of local anesthetic. The outer end of the tube has a capped (5) Luer locking adapter (4) which will securely accept a syringe containing local anesthetic. The inner end of this local anesthetic bearing lumen (12) has several small openings (10) on the anterior aspect of the distal 11 cm of tube corresponding to the anatomical position of the epiglottis, larynx and trachea. Injection down this lumen (12) would therefore evenly distribute anesthetic solution on these pain sensitive structures.

I claim:

1. An endotracheal tube capable of administering a local anesthetic comprising:
    (a) a tubular member for ventilating a patient, said tubular member having an arcuate shape, an interior, a proximal end and a distal end;
    (b) a first conduit associated with the tubular member for carrying a local anesthetic, said first conduit sealed from fluid communication with the interior of said tubular member;
    (c) first aperture means extending along a portion of the length of the tubular member and in fluid communication with the first conduit for permitting local anesthetic to be sprayed radially inwardly of the arcuate shape along the larynx, trachea and epiglottis of a patient when the endotracheal tube is in its operable position, said first aperture means comprising a plurality of apertures extending longitudinally along a portion of the length of the tubular member said first aperture means being sealed from fluid communication with the interior of said tubular member;
    (d) inflatable means connected to the tubular member and located in the vicinity of the distal end for providing an air-tight seal of the trachea, said inflatable means comprising an inflatable cuff and said first aperture means being positioned between the inflatable cuff and the proximal end of the tubular member;
    (e) second aperture means in fluid communication with the first conduit, said second aperture means being located between the distal end of the tubular member and the inflatable means for permitting local anesthetic to be sprayed inwardly of the arcuate shape along the trachea of the patient, said second aperture means being sealed from fluid communication with the interior of said tubular member; and (f) a second conduit associated with the tubular member and in fluid communication with the interior of the inflatable means.

2. An endotracheal tube capable of administering a local anesthetic comprising:

(a) a tubular member for ventilating a patient, said tubular member having an arcuate shape, an interior, a proximal end and a distal end;

(b) a first conduit associated with the tubular member for carrying a local anesthetic, said first conduit sealed from fluid communication with the interior of said tubular member;

(c) first aperture means extending along a portion of the length of the tubular member and in fluid communication with the first conduit for permitting local anesthetic to be sprayed radially inwardly of the arcuate shape along the larynx, trachea and epiglottis of a patient when the endotracheal tube is in its operable position, said first aperture means comprising a plurality of apertures extending longitudinally along a portion of the length of the tubular member said first aperture means being sealed from fluid communication with the interior of said tubular member;

(d) inflatable means connected to the tubular member and located in the vicinity of the distal end for providing an air-tight seal of the trachea, said inflatable means comprising an inflatable cuff and said first aperture means being positioned between the inflatable cuff and the proximal end of the tubular member;

(e) second aperture means in fluid communication with the first conduit, said second aperture means being located between the distal end of the tubular member and the inflatable means for permitting local anesthetic to be sprayed inwardly of the arcuate shape along the trachea of the patient, said second aperture means being sealed from fluid communication with the interior of said tubular member wherein the first aperture means and the second aperture means are located within 11 centimeters of the distal end of the tubular member so that when the endotracheal tube is in position in a patient, local anesthetic passing through the first aperture means and the second aperture means initially flows in an anterior direction and contacts the epiglottis, larynx and trachea of the patient; and (f) a second conduit associated with the tubular member and in fluid communication with the interior of the inflatable means.

* * * * *